United States Patent [19]

Storet

[11] Patent Number: 5,463,153
[45] Date of Patent: Oct. 31, 1995

[54] PROCESS FOR PREPARING 1-CHLORO-1,3-BUTADIENE

[75] Inventor: Isabelle Storet, Les Eparres, France

[73] Assignee: Enichem Elastomeres France S.A., Courbevoie, France

[21] Appl. No.: 307,425

[22] Filed: Sep. 19, 1994

[30] Foreign Application Priority Data

Sep. 19, 1993 [FR] France ................... 93 11304

[51] Int. Cl.$^6$ ................................................ C07C 21/00
[52] U.S. Cl. ................................................ 570/227; 570/228
[58] Field of Search ................................................ 570/227, 228

[56] References Cited

U.S. PATENT DOCUMENTS 3,435,083  3/1989  Baader et al. .
3,481,994  12/1969  Lutz ................................................ 570/227

FOREIGN PATENT DOCUMENTS 0372183  9/1989  European Pat. Off. .
0775101  10/1980  U.S.S.R. ................................................ 570/227

*Primary Examiner*—Alan Siegel
*Attorney, Agent, or Firm*—Burns, Doane, Swecker & Mathis

[57] ABSTRACT

Process for preparing 1-chloro-1,3-butadiene, which consists in gas-phase dehydrochlorinating a dichlorobutene selected from 3,4-dichloro-1-butene and 1,4-dichloro-2-butene, in the presence of a catalyst selected from lanthanum phosphate and lanthanum phosphate doped with an alkali or alkaline-earth metal.

4 Claims, No Drawings

PROCESS FOR PREPARING 1-CHLORO-1,3-BUTADIENE

The present invention relates to a process for preparing 1-chloro-1,3-butadiene by means of the dehydrochlorination of 3,4-dichloro-butene-1 and/or 1,4-dichloro-2-butene.

It is known that 1-chloro-1,3-butadiene, also referred to as "alpha-chloroprene", can be polymerized or copolymerized, preferably with chloroprene (2-chloro-1,3-butadiene).

Alpha-chloroprene is normally found as a byproduct from most reactions leading to 2-chlorobutadiene. In fact, small amounts of alpha-chloroprene are formed during vinylacetylene hydrochlorination. Furthermore, amounts of alpha-chloroprene, which may vary as a function of the existing reaction conditions, are formed during the reactions of butadiene chlorination, or of 1,4-chloro-2-butene isomerization to yield 3,4-dichloro-1-butene, or, also, of 3,4-dichloro-1-butene dehydrochlorination.

A high yield in alpha-chloroprene can be obtained by dehydrochlorinating 1,4-dichloro-2-butene, obtained in its turn by starting from butenediol, with sodium amide in mineral oil. Such a process is very expensive, because it requires at least stoichiometric amounts of sodium amide.

The object of the present invention is an improved process for producing 1-chloro-1,3-butadiene, which overcomes the above drawbacks.

In accordance with the above, the present invention relates to a process for preparing 1-chloro-1,3-butadiene, characterized in that a dichlorobutene selected from 3,4-dichloro-1-butene, 1,4-dichloro-2-butene and their mixtures, is dehydrochlorinated, in gas phase, in the presence of a catalyst selected from lanthanum phosphate, lanthanum phosphate doped with at least one alkali or alkaline-earth metal, and mixtures of said phosphates.

The catalyst is preferably selected from lanthanum phosphate and lanthanum phosphate doped with cesium.

By "lanthanum phosphate doped with an alkali or an alkaline-earth metal", a compound is understood herein which is as defined in EP-A-440 555, i.e., a compound having the general formula (based on dry material):

$$LaPO_4 \cdot (Imp)_p \qquad (I)$$

In the compound having the above general formula (I), by "Imp", a basic impregnation compound is understood, which is constituted by a metal selected from alkali metals or alkaline-earth metals, preferably alkaline-earth metals, with said metals being associated with a counter ion, to such an extent as to secure the neutrality of the compound of general formula (I). In above formula (I), the coefficient "p" is comprised within the range of from $10^{-2}$ to $\frac{1}{3}$, preferably of from 0.05 to 0.2.

Lanthanum phosphate can be prepared according to well-known techniques, e.g., by reacting phosphoric acid and a lanthanum salt, e.g., lanthanum carbonate.

The preparation of lanthanum phosphate doped with an alkali metal or an alkaline-earth metal is disclosed in EP-A-440 555.

Before being used in the dehydrochlorination process according to the present invention, the catalyst is submitted to the usual calcination procedures, preferably at temperatures comprised within the range of from 420° to 480° C.

The catalyst can be used in the process of the present invention as such, or as a combined form with inert solid materials acting as binding agents. For such a purpose, such oxides as silica, alumina, titania, magnesia, zirconia, taken either alone or combined with each other, proved to be advantageously suitable.

The catalyst and the binding agent can be mixed in a mutual weight ratio of 30:70, preferably comprised within the range of from 50:50 to 70:30. The resulting mixture can be given a desired end shape, e.g., they can be given the shape of extruded bodies or pellets.

The dehydrochlorination reaction, on which the process according to the present invention is based, probably proceeds according to the following mechanism:
— isomerization of 3,4-dichloro-1-butene (3,4-DCB), yielding 1,4-dichloro-1-butene (1,4-DCB);
— dehydrochlorination of 1,4-DCB to yield 1-chloro-1,3-butadiene (1-CB).

It derives from the above that the process according to the present invention is equally effective by starting from both 3,4-DCB and 1,4-DCB.

The process according to the present invention is carried out by causing 3,4-DCB, or 1,4-DCB, or mixtures thereof, to flow over the above catalyst.

According to an embodiment, a gas carrier can be used, which is constituted by one or more inert gas(es) under the reaction conditions, preferably nitrogen.

The contact time is generally comprised within the range of from 5 to 0.5 seconds, preferably of from 2 seconds to 1 second.

The process according the present invention is advantageously carried out at temperatures comprised within the range of from 190° to 280° C., preferably of from 200° to 250° C.

The following examples are reported in order to illustrate the present invention in greater detail.

EXAMPLE 1

Preparation of LaPO$_4$ 57 g of H$_3$PO$_4$ (85%, Prolabo) and 150 ml of deionized water are charged to a reactor. The resulting mixture is kept stirred at 500–700 rpm (revolutions per minute). An amount of 166.6 g of La$_2$(CO$_3$)$_3$·12H$_2$O is slowly added, when cold, with strong stirring. The reaction medium is heated during 60 minutes, and is then cooled down to room temperature during 30 minutes. The suspension is filtered on a No. 3 glass frit filter until mother liquors are exhausted.

The filter cake is dispersed in 1000 ml of water, with strong stirring, and is kept suspended for 30 minutes, with simultaneously being stirred. The washing step is repeated twice. The product is filtered, then is dried at 110° C.

EXAMPLE 2

Preparation of cesium-doped LaPO$_4$ 4.7 ml of 6M CsOH is added to 14.12 ml of 1 M H$_3$PO$_4$. The mixture is adjusted at a volume of 50 ml by adding water.

To 50 g of LaPO$_4$ prepared according to the preceding example, 20 ml of the above solution is added dropwise.

The product is left standing for 60 minutes, is dried overnight at 110° C., then is fired at 500° C. during 120 minutes.

The dry product contains 3% of cesium (by weight/weight).

EXAMPLE 3

General Experimental Procedure

To a tubular quartz reactor equipped with a thermometer well, two fittings for fluid feed (nitrogen, syringe push medium) and a cylindrical oven, a layer of pyrex glass powder (1 cm), a layer of the catalyst mixture (2 ml)—pyrex powder (8 g), a layer of pyrex beads (2 cm), are charged in sequence onto the glass frit septum.

The catalyst is conditioned as follows:

—calcination: 120 minutes at 400° C.;

—heat conditioning: 120 minutes at 250° C.

The resulting reaction products are separated by means of a trap (with they being isolated inside three traps installed in cascade); said separation is carried out during a time period of 1 hour after a starting-up period of 45 minutes.

Experimental conditions:

—$N_2$: 2,8 l/h

—3,4-dichlorobutene (indicated, in short form, as "3,4-") or 1,4-dichloro-2-butene feed rate: g/h;

—temperature: 250° C.

The results are reported in Table 1, in which:

$RR_{1CB}$ is the yield of 1-chlorobutadiene, $RR_{1,4}$ is the yield of 1,4-dichloro-2-butene, $TT_{3,4}$ is the 3,4-dichloro-1-butene conversion, $TT_{1,4}$ is the 1,4-dichloro-2-butene conversion.

TABLE 1

| Substitution positions | Catalyst | $RR_{1,CB}$ | $RR_{1,4}$ | $TT_{3,4}$ | $TT_{1,4}$ |
|---|---|---|---|---|---|
| 3,4- | Example 1 | 70% | 8% | 86% | — |
| 3,4- | Example 2 | 57% | 10% | 87% | — |
| 1,4- | Example 2 | 79% | — | — | 100% |

EXAMPLE 4

In this Example (Table 2), the effect was studied of temperature of the reaction of 3,4-dichlorobutene dehydrochlorination to yield 1-chlorobutene in the presence of $Cs_2HPO_4 \cdot LaPO_4$, prepared as disclosed in above Example 2. Also computed was the yield of chloroprene ($RR_{CP}$).

TABLE 2

| Temperature | $RR_{CP}$ | $RR_{ICB}$ | $RR_{1,4}$ | $TT_{3,4}$ |
|---|---|---|---|---|
| 250° C. | 0 | 57% | 10% | 87% |
| 200° C. | 0 | 67% | 8% | 93% |
| 180° C. | 0 | 13% | 22% | 35% |

The data reported in Table 2 shows that the best result in terms of conversion rate and yield are obtained at about 200° C., even if the data at 250° C. is still satisfactory.

I claim:

1. Process for preparing 1-chloro-1,3-butadiene, characterized in that a dichlorobutene selected from 3,4-dichloro-1-butene, 1,4-dichloro-2-butene and their mixtures, is dehydrochlorinated in gas phase, in the presence of a catalyst selected from lanthanum phosphate, lanthanum phosphate doped with at least one alkali or alkali-earth metal, and mixtures of said phosphates.

2. Process according to claim 1, characterized in that the catalyst is selected from lanthanum phosphate and lanthanum phosphate doped with cesium.

3. Process according to claim 1, characterized in that the reaction temperature is comprised within the range of from 190° to 280° C.

4. Process according to claim 3, characterized in that the reaction temperature is comprised within the range of from 200° to 250° C.

\* \* \* \* \*